United States Patent [19]

Miles

[11] Patent Number: 4,817,625
[45] Date of Patent: Apr. 4, 1989

[54] SELF-INDUCTANCE SENSOR

[75] Inventor: Laughton E. M. Miles, Palo Alto, Calif.

[73] Assignees: Laughton Miles; Zeala Miles, both of Palo Alto, Calif.

[21] Appl. No.: 42,140

[22] Filed: Apr. 24, 1987

[51] Int. Cl.[4] ................................................ A61B 5/08
[52] U.S. Cl. .................................... 128/721; 128/725; 128/782; 33/179
[58] Field of Search ....................... 128/721, 725, 782; 33/176, 179

[56] References Cited

U.S. PATENT DOCUMENTS 3,560,845  2/1971  Goldberg et al. ..................... 324/34
4,308,872  1/1982  Watson et al. ....................... 128/725
4,373,534  2/1983  Watson ................................. 128/725

FOREIGN PATENT DOCUMENTS 2116725  9/1983  United Kingdom ................. 128/721

OTHER PUBLICATIONS

Milledge, J. S., and Stott, F. D., "Inductive Plethysmography-a New Respiratory Transducer", Proceedings of the Physiological Society, Jan. 1977, pp. 4–5.
Shapiro, A. and Cohen, H. D., (1965), "Transactions of the New York Academy of Science", vol. 27, pp. 634–649.
Konno, K. and Mead, J., (1967), "Journal of Applied Physiology", Vol. 22, pp. 407–422.

Primary Examiner—Edward M. Coven
Assistant Examiner—Randy Citrin
Attorney, Agent, or Firm—Townsend and Townsend

[57] ABSTRACT

The self-inductance sensor disclosed includes a band of distensible material, and a strap of nondistensible material which form in combination a closed loop which circumscribes the object. A conductor is secured to the band of distensible material. The conductor includes two portions each extending from one end of the band to the other and having an irregular repetitive configuration. The conductor portions are symmetrically juxtaposed to one another to form a series of substantially enclosed areas which change shape as the band is distended. The self-inductance of the conductor is measured to indicate the relative extension of the band and thus the change in circumference of the object.

11 Claims, 1 Drawing Sheet

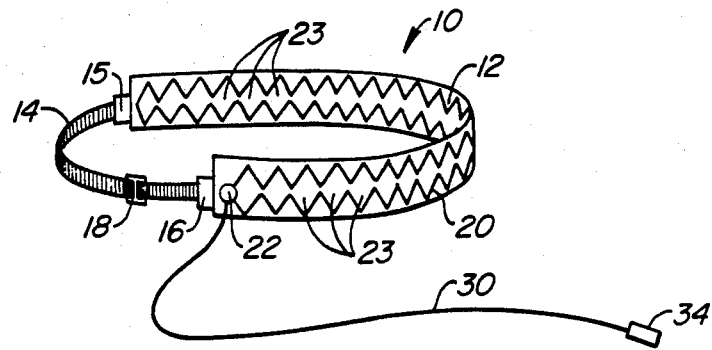
FIG._1.
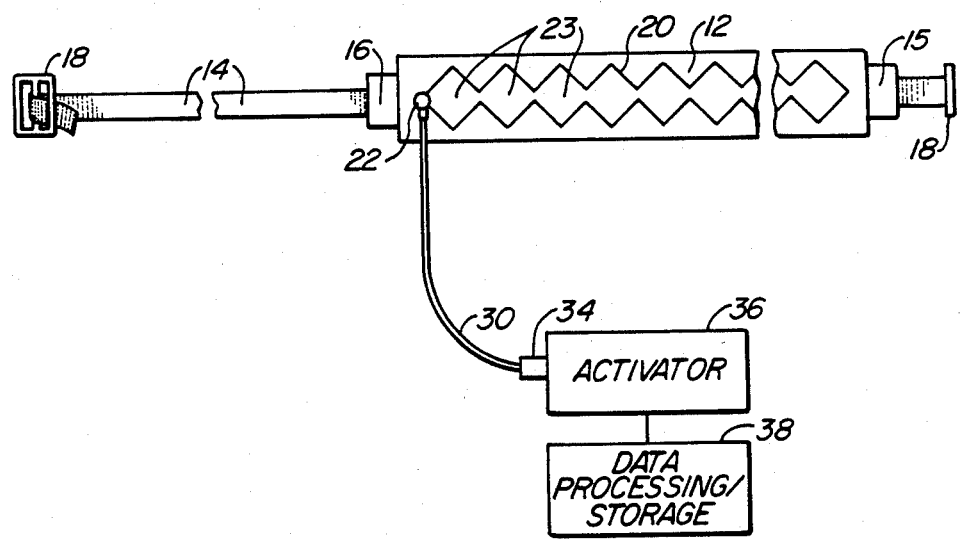
FIG._2.
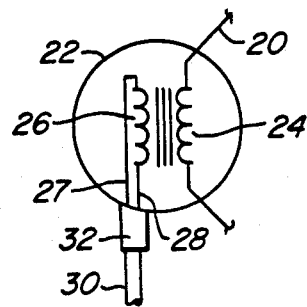
FIG._3.

SELF-INDUCTANCE SENSOR

BACKGROUND OF THE INVENTION

The present invention relates to an improved self-inductance sensor used for measuring the change in circumference of an object.

The field of plethysmography, i.e., the study of the change in size of an organ or limb, often employs inductive sensors as the measuring device. A variety of such sensors have been disclosed in various patents to Goldberg et al., including U.S. Pat. No. 3,560,845. The use of such a sensor to measure cross-sectional area changes in the torso, and thus respiration volume, has been discussed in Milledge, J.S., and Stott, F.D., "Inductive Plethysmography -- A new Respiratory Transducer", *Proceedings of the Physiological Society,* January 1977, pages 4–5. By measuring the simultaneous changes in airflow, the changes in the signals from various types of chest and abdominal respiration sensors can be weighted and summed in order to provide an independent measurement of respiration volume. Such calibration procedures were described by Shapiro, A. and Cohen, H.D. (1965) "Transactions of the New York Academy of Science", Vol. 27, page 634. Such techniques were further explored in Konno, K. and Mead, J.(1967) "Journal of Applied Physiology", Vol 22, page 407. In U.S. Pat. Nos. 4,308,872 and 4,373,534 Watson et al. further describe the use of inductive plethysmography sensors which measure cross-sectional area.

The use of an inductive sensor which circumscribes the torso has been found to have certain inherent disadvantages. In theory, an inductive sensor which fully encircles the torso is advantageous in respiration plethysmography because it measures cross-sectional area, not circumference, and it is that area which is directly proportional to respiration volume. However, sensors containing conductors which fully circumscribe the entire torso are subject to error from calibration inaccuracies, displacement of the sensor, deformation of the sensor for reasons other than respiration, and changes in output due to different body positions. These errors tend to be of greater magnitude than any errors due to measuring cross-sectional area rather than circumference. Also, to complete the current loop, electrical connections must be made to the conductor at each end each time that the sensor is placed on the patient. This is a difficult and cumbersome procedure which is subject to frequent failure, and requires the use of a sensor fitted to the size of the patient.

SUMMARY OF THE INVENTION

The present invention provides a self-inductance sensor which includes a band of distensible material, and a strap of nondistensible material. The band and strap in combination form a closed loop which circumscribes the object to be measured. A conductor is secured to the band of distensible material. The conductor includes two portions each extending the length of the band. The conductor portions each have a repetitive irregular configuration, and the two portions are symmetrically juxtaposed to form a series of substantially enclosed areas. The areas change shape as the band is distended, which changes the self-inductance of the conductor. The self-inductance of the conductor is measured to indicate the relative extension of the band and thus the change in circumference of the object about which the sensor has been placed.

While measurement of circumference is less accurate than a cross-sectional area measurement in theory in respiration plethysmography, the sensor of the present invention appears to be equally as accurate and far more efficient than an area sensor in practice. The sensor of the present invention can be attached more easily and reliably to the patient because the attachment is performed with nondistensible material, typically a narrow fabric strap. While various techniques may be used to measure self-inductance, in the preferred embodiment of the present invention, a coil is an integral part of the closed loop conductor. A single cable can be permanently fixed to a small transformer which activates the coil of the conductor. The conductor is located only on the distensible portion of the sensor, and provides a permanently closed current path which does not have to be closed when the sensor is placed on the patient. The short conductor length and closed conductor path appear to make the sensor of the present invention much more reliable than a crosssectional area sensor, and the short conductor path appears to make the sensor less sensitive to movement artefact.

The novel features which are characteristic of the invention, both as to organization and method of operation, together with further objects and advantages thereof will be better understood from the following description considered in connection with the accompanying drawings in which a preferred embodiment of the invention is illustrated by way of example. It is to be expressly understood, however, that the drawings are for the purpose of illustration and description only and are not intended as a definition of the limits of the invention.

BRIEF DESCRIPTION OF THE DRAWINGS

FIG. 1 is a perspective view of a preferred embodiment of the sensor of the present invention;

FIG. 2 is a plan view of the preferred embodiment of FIG. 1;

FIG. 3 is an enlarged schematic view of the transformer of the embodiment of FIGS. 1 and 2.

DESCRIPTION OF THE PREFERRED EMBODIMENT

A preferred embodiment 10 of the sensor of the present invention is illustrated generally by way of reference to FIGS. 1 and 2. The sensor includes a band 12 of distensible material, typically an elastic material with vertical Nylon stiffeners, plus a nondistensible strap 14 of a conventional cloth fabric. A pair of seams 15, 16, attach the ends of strap 14 to the ends of band 12. A buckle or similar connector 18 is located intermediate strap 14 so that sensor 10 can be fastened to the patient. The location of buckle 18 on strap 14 is adjustable so that sensor can fit a variety of patients. In respiration plethysmography, a pair of such sensors are typically employed, one about the chest and one about the abdomen.

A conductor 20 and transformer 22 are sewn to distensible strap band 12. In the embodiment shown, conductor 20 comprises a closed loop emanating from transformer 22 from one end of distensible strap 12 to the other and back again. Conductor 12 includes two symmetric portions each having a sawtoothed configuration and juxtaposed to one another. The respective portions of the conductor form a plurality of substantially enclosed diamond shaped areas 23. The conductor portions may take on a geometric shape other than the sawtoothed configuration shown, but the juxtaposed portions must form a series of substantially enclosed geometrically shaped areas. The change in shape of areas 23 results in a change in the self-inductance of the conductor.

Transformer 22 is illustrated in more detail by way of reference to FIG. 3. Conductor 20 includes a coil 24 within transformer 22, which serves as the primary coil of the transformer. Secondary coil 26 has a pair of leads 27, 28 hard wired to a coaxial cable 30. A bracket 32 permanently fixes coaxial cable 30 to transformer 22, and a single connector 34 at the distal end of cable 30 (see FIG. 2) attaches the sensor to a data processor or storage device 38 and activating circuitry 36 which provides the alternating current used to excite coil 24. The alternating current from circuitry 36 is passed through cable 30 to induce a corresponding current in conductor 20. The phase shift in the current in cable 30 as it passes through coil 26 is indicative of the self-inductance of the activated conductor 20.

In operation, sensor 10 is employed in respiration plethysmography by locating a pair of sensors about the chest and abdomen of the patient, and fixing the sensors to the patient using buckles 18. As the patient breathes, distensible bands 12 will expand and contract. An alternating current in each secondary coil 26 of each transformer 22 causes a current to flow in the primary coils 24. The self-inductance in conductors 20 caused by the alternating current changes as the bands 12 are distended and areas 23 change shape. This change in inductance is sensed through transformers 22, typically in the form of a change in the frequency of the induced alternating current, or in the form of a change in the phase of a phase-shift network. Connectors 34 are attached to activating circuitry, 36 which is in turn connected to a data processing device or a data recorder, 38 which weights, sums and calibrates the data from chest and abdominal sensors to derive respiration volume.

While a preferred embodiment of the present invention has been illustrated in detail, it is apparent that modifications and adaptations of that embodiment will occur to those skilled in the art. In particular, while the invention has been described in terms of a respiration sensor, it is apparent that the sensor would be used in measuring the variable circumference of a wide variety of objects. It is to be expressly understood that such modifications and adaptations are within the spirit and scope of the present invention, as set forth in the following claims.

What is claimed is:

1. A self-inductance sensor for measuring the change in circumference of an object comprising:
   an elongate band of distensible material adapted to partially circumscribe the object;
   an elongate strap of nondistensible material having its ends attached to the opposite ends of the band so that the band and strap in combination form a closed loop adapted to completely circumscribe the object;
   an electrical conductor secured to the band and having a first portion extending from a first position adjacent one end of the band to a second position adjacent the other end of the band and a second portion extending from said second position to said first position, each portion of the conductor having a repetitive geometric configuration with the portions symmetrically and closely juxtaposed to form a series of substantially enclosed areas which change shape as the band is distended; each of said substantially enclosed areas being bounded half by said geometric configuration of said first position and half by said geometric configuration of said second portion;
   and means for measuring the self-inductance of the conductor to indicate the relative extension of the band and thus the change in circumference of the object.

2. The sensor of claim 1 wherein the portions of the conductor each have a sawtoothed configuration, and the portions define a series of substantially enclosed diamond shaped areas between the respective portions which change shape as the band is distended.

3. The sensor of claim 1 wherein the strap is separated into sections, and additionally comprising a buckle releasably connecting the sections of the strap together to form a continuous loop adapted to be placed about the object to be measured.

4. The sensor of claim 1 wherein the measuring means includes a first coil interposed in the conductor, and a second coil located proximate the first coil.

5. The sensor of claim 4 wherein the measuring means includes means for measuring the phase shift in an alternating current passed through the second coil to activate the conductor.

6. The sensor of claim 4 wherein the measuring means includes a single cable non-removably attached to the second coil.

7. The sensor of claim 4 wherein the conductor, including the first coil, is continuous.

8. The sensor of claim 4 wherein the first coil is located at said one end of the band.

9. A self-inductance sensor for measuring the change in circumference of an object comprising:
   a band of distensible material;
   a strap of nondistensible material attached to the opposite ends of the band, said strap being separated into sections;
   means for adjustably fastening the separate sections of the strap together so that the strap and band in combination form a closed loop adapted to circumscribe the object;
   a continuous electrical conductor secured to the band and having a first portion extending from a first position adjacent one end of the band to a second position adjacent the other end of the band, a second portion extending from said second position to said first position, each portion of the conductor symmetrically juxtaposed to define a plurality of substantially enclosed diamond shaped areas between the respective portions which change shape as the band is distended, and a first coil intermediate the first and second portions;
   a second coil proximate the first coil; and
   means coupled to the second coil for measuring the self-inductance of the conductor to indicate the relative extension of the band and thus the change in circumference of the object.

10. The sensor of claim 9 wherein the measuring means includes a single cable non-removably attached to the second coil.

11. The sensor of claim 9 wherein the measuring means includes means for passing an alternating current through the second coil, and means for measuring the phase shift of the alternating current.

* * * * *